United States Patent [19]

Heinrich et al.

[11] Patent Number: 5,193,285
[45] Date of Patent: Mar. 16, 1993

[54] MECHANICAL SHAPE SENSOR AND DATA RECORDER

[75] Inventors: Michael Heinrich, Chicago; Eric-Jan Ginder, Oak Park, both of Ill.

[73] Assignee: Pin Dot Products, Niles, Ill.

[21] Appl. No.: 739,110

[22] Filed: Aug. 1, 1991

[51] Int. Cl.$^5$ .............................................. G01B 5/20
[52] U.S. Cl. .................. 33/514.2; 33/561.1; 33/578; 128/774; 346/50; 346/104
[58] Field of Search ................ 33/561.1, 561.2, 561.3, 33/512, 514.2, 515, 551, 552, 553, 554, 574, 578, 32.3, 32.7; 73/172; 128/774, 779, 780, 781; 346/33 R, 40, 50, 104

[56] References Cited

U.S. PATENT DOCUMENTS

| | | |
|---|---|---|
| 1,830,648 | 11/1931 | Engel . |
| 2,162,916 | 6/1939 | Hyland . |
| 2,378,039 | 6/1945 | Schenker . |
| 3,134,635 | 5/1964 | Minter ................. 346/104 |
| 3,264,382 | 8/1966 | Angell et al. . |
| 3,286,272 | 11/1966 | Dege et al. ............. 346/50 |
| 3,458,898 | 8/1969 | Casparis . |
| 3,709,144 | 1/1973 | Sims ..................... 346/104 |
| 3,830,896 | 8/1974 | Flicker et al. . |
| 4,046,611 | 9/1977 | Sanson . |
| 4,413,540 | 11/1983 | Burge . |
| 4,454,090 | 6/1984 | Saumell . |
| 4,470,782 | 9/1984 | Zimmerman, Jr. et al. . |
| 4,493,877 | 1/1985 | Burnett . |
| 4,525,130 | 6/1985 | Netznik . |
| 4,615,856 | 10/1986 | Silverman . |
| 4,637,789 | 1/1987 | Netznik . |
| 4,697,240 | 9/1987 | Cedar et al. . |
| 4,728,150 | 3/1988 | Gaudreau, Jr. ........... 33/515 |
| 4,867,922 | 9/1989 | Zuccato . |
| 4,876,758 | 10/1989 | Rolloff et al. . |
| 4,890,235 | 12/1989 | Reger et al. . |
| 4,959,909 | 10/1990 | Wong .................. 33/561.1 |
| 4,998,354 | 3/1991 | Silverman et al. . |
| 5,060,393 | 10/1991 | Silverman et al. ....... 33/515 |

FOREIGN PATENT DOCUMENTS

| | | |
|---|---|---|
| 0285989 | 10/1988 | European Pat. Off. ....... 33/512 |
| 0281493 | 1/1915 | Fed. Rep. of Germany . |
| 0907977 | 3/1946 | France ........................ 33/512 |

OTHER PUBLICATIONS

*The Chicago Insert: An Approach to Wheelchair Seating for the Maintenance of Spinal Posture in Duchenne Muscular Dystrophy*, Siegel et al., pp. 27-29, (date unknown).

(List continued on next page.)

Primary Examiner—William A. Cuchlinski, Jr.
Assistant Examiner—Alvin Wirthlin
Attorney, Agent, or Firm—Emrich & Dithmar

[57] ABSTRACT

A mechanical shape sensor measures and provides a two-dimensional representation of the contour of a person's thighs and buttocks or the dorsal and lateral surfaces of a person's trunk for facilitating the fabrication of custom contoured seat cushions such as for use in a wheelchair. The mechanical shape sensor is integrated in a chair-like base capable of multiple adjustments to accommodate a range of dimensions and sizes of persons being measured. The mechanical shape sensor converts the three-dimensional contoured support surface of a person seated on an array of movable support elements into a two-dimensional format which is recorded on a data sheet in a form which is easily transmitted via telecommunications link to a central locatin for fabricating a custom contoured seat cushion. Each of the moveable support elements is coupled to a position marker in the data recorder. The position markers are disposed adjacent a pressure-sensitive data sheet inserted in the data recorder for engaging the data sheet and imprinting data points thereon when urged toward the data sheet by an impression-forming mechanism comprised of a pair of opposed rollers which are manually displaced in unison over the position markers. Each data point represents the depth of contour of the seat cushion at a given location with a person seated thereon. The data sheet is then removed from the data recorder for use in fabricating a custom contoured seat cushion.

37 Claims, 4 Drawing Sheets

OTHER PUBLICATIONS

*Hip Angle and Upper Extremity Movement Time in Children with Cerebral Palsy*, Nwaobi et al., Resna 8th Annual Conference/Memphis, Tn., pp. 39–41 (1985).

*Instrumented, Adjustable Seat for Evaluating Posture and Body Contours*, Reger et al., pp. 335–337, RESNA 8th Annual Conference/Memphis, TN., (1985).

*Shape and Pressure Distribution on Wheelchair Cushions*, Reger et al., pp. 341–343, RESNA 8th Annual Conference/Memphis, TN, (1985).

*Weightbearing Tissue Contour and Deformation by Magnetic Resonance Imaging*, Reger et al., pp. 387–389, RESNA 9th Annual Conference/Minneapolis, MN, (1986).

*Research and Development Considerations and Engineering Perspective*, Douglas A. Hobson, Clinical Prosthetics and Orthotics, vol. 10, No. 4, pp. 122–129 (1986).

*Computer Aided Prescription of Specialized Seats for Wheelchairs*, Reger et al., Advances in External Control of Human Extremities IX, pp. 559–562, (1987).

*Analysis of Compression, Shear and Surface Tension on Seat Cushions*, Chung et al., RESNA 10th Annual Conference/San Jose, CA, pp. 269–271 (1987).

*Comparative Evaluation of Pressure Distribution on Flat Forms and Contoured Cushions*, Chung et al., pp. 323–325, RESNA 10th Annual Conference/San Jose, CA (1987).

*Body Contours and Pressure Distributions of Normal and SCI Subjects on Wheelchair Cushions*, Chung et al., pp. 515–517, RESNA 10th Annual Conference/San Jose, CA (1987).

*Clinical Application of the Adjustable "Computer Chair"*, McGrew et al., pp. 568–570, RESNA 10th Annual Conference/San Jose, CA (1987).

*Design of a Computer Aided Manufacturing System for Custon Contoured Wheelchair Cushions*, Brienza et al., ICAART 88–Montreal, pp. 312–313 (1988).

*Effect of Contoured Support Surface on Pressure Distribution*, Chung et al., pp. 314–315, ICAART 88–Montreal (1988).

MECHANICAL SHAPE SENSOR AND DATA RECORDER

FIELD OF THE INVENTION

This invention relates generally to the fabrication of seat cushions and is particularly directed to apparatus for measuring and recording an impression of a person's seat contact contour, i.e., buttocks and thighs as well as dorsal and lateral trunk surfaces, for fabricating a custom contoured seat cushion.

BACKGROUND OF THE INVENTION

Recent advances in rehabilitation technology have improved the products available which cushion and support a person while seated. Maintaining a functional seated posture for a long period of time requires special support particularly for the elderly who incur more than 70% of reported pressure sores. Pressure sores arise from bony protuberances which cause areas of excessive pressure restricting blood flow to the surrounding tissue. In order to avoid pressure sores, the person must be frequently moved in those areas to which blood circulation has been restricted and massaged in attempting to prevent the formation of an ulcer. Appropriate body support is required to provide protection from this type of tissue trauma, prevent poor posture and enhance functional capabilities of those restricted to the seated posture.

Custom contoured cushions have been recognized as providing the support and comfort necessary for those who remain seated for extended periods. Various approaches have been undertaken to fabricate user contoured seat cushions which provide the desired support and comfort. One approach makes use of several aluminum templates which provide support and which are bendable to form a contoured support surface. This approach not only requires a separate cushion to be placed over the contoured support surface, but also provides a support surface which generally only remotely approaches the seating support surface contour of a user because of the difficulty in manually bending the aluminum plates to match the user's contour. Another approach employs a wooden frame having a plurality of apertures into which dowels are inserted in a snugly fitting manner. Each of the dowels may be chiseled down to a given length to match the support surface of an intended user. Upholstery including padding is then positioned over and in contact with the dowel ends to provide a continuous contoured seating surface. This approach is time consuming, expensive and generally unpredictable.

Yet another approach to forming a contoured seating cushion employs a flexible bag containing a granular material and fitted with a valve so that the bag can be maintained in a condition evacuated of air. The bag in its non-evacuated state is pushed against one who is to be supported and the granular material flows to allow the bag to take a shape closely conforming to the user's shape. The bag is then evacuated through the valve, causing the granular material to become pressed by virtue of the resulting pressure differential across the wall of the bag. The previously flexible support device thus becomes rigid, with the granular material becoming locked into a rigid support mass in a shape conforming to the shape of the body being supported. One problem with this approach is in the requirement for maintaining the bag in an evacuated condition for extended periods of time. As the bag becomes evacuated, or the vacuum is otherwise lost, conformance of the bag to the shape of a user is also lost.

Another approach, such as disclosed in U.S. Pat. No. 4,615,856 to Silverman, also employs bead-filled bags to make an impression of the seat and back portions of an intended user by evacuating the bags attached to a molding frame. A positive mold of the individual's respective backside and buttocks impressions are made, which is then utilized with another apparatus to mold a custom fitted seat cushion. Although capable of accurately contouring the cushions to an intended user's contour, this approach requires a rather expensive air bag fitted molding frame operated by one with specialized training.

Yet another approach creates a computer model of the cushion contours from data obtained through a contour measurement process which employs contour gauges designed to detect tissue deflection and contact with regular foam cushions. Data reflecting the pressure at the body-cushion interface is then used by the computer to control a three-dimensional milling machine for cutting out the cushion from a foam plastic blank. This approach requires sophisticated and expensive equipment used by one with special training in its control and operation.

Still another approach is disclosed in U.S. Pat. No. 4,998,354 to Silverman et al. which measures the three-dimensional contour of a person's thighs and buttocks as well as one's dorsal and lateral trunk surfaces for providing a two-dimensional representation of this contoured surface to facilitate fabrication of custom contoured seat cushions. This mechanical shape sensor is a stand alone unit incorporating a plurality of spaced flexible, incompressible cables having a first end disposed in an upper surface of a compressible, resilient support element and a second end having a position marker thereon. With one seated on the array of resilient support elements, the first ends of the cables form a matching contoured surface, while the second ends of the cables provide a two-dimensional graphic representation of the contoured surface, where the second end portions of the cables are arranged in a cyclic manner in accordance with the number of support elements in a given row within the matrix of support elements. Contour data is recorded on a medium such as carbon paper by displacing a roller over positioning indicators located on the second end of each of the cables.

The present invention represents an improvement over all of the prior art approaches discussed above in terms of enhanced contour surface measurement accuracy and the recording of data in a more readily usable form.

OBJECTS AND SUMMARY OF THE INVENTION

Accordingly, it is an object of the present invention to provide an improved apparatus and method for measuring and recording the surface contour of a person's thighs and buttocks as well as dorsal and lateral trunk surfaces.

It is another object of the present invention to provide a low cost, portable, easily used, mechanical shape sensor and data recorder for measuring and recording the contour of a person's seating support surface for use in fabricating custom contoured seat cushions.

Yet another object of the present invention is to provide an arrangement and method for measuring the shape of the buttock-cushion interface, recording this contour information in a format readily transmitted via telecommunications link to a remote fabrication facility, and fabricating a seat cushion having a support surface contoured in accordance with the buttock-cushion interface measurement.

A further object of the present invention is to convert the measurement of a three-dimensional contoured surface to a two-dimensional graphic representation for use in forming a support cushion having the measured contoured surface.

A still further object of the present invention is to provide a mechanical arrangement for recording data points on a pressure-sensitive data form which applies a uniform pressure which is operator independent to all points on the form for highly accurate data recording.

Another object of the present invention is to provide a system for measuring and recording various dimensions of a person in the seated position such as on a chair including the surface contour of the person's thighs and buttocks as well as dorsal and lateral trunk surfaces.

Yet another object of the present invention is to provide a highly accurate arrangement for measuring and recording the three-dimensional contour of a surface in two-dimensional graphic form comprised of a plurality of data points.

A further object of the present invention is to provide a manual, applied pressure type of data recording arrangement in which the pressure applied to the data sheet is independent of the force required to operate the mechanism.

This invention contemplates apparatus for measuring and recording the contour of a person's seating support surface, the apparatus comprising: a chair-like base having a seat portion and a back portion for respectively supporting a person's thighs and buttocks and a person's back when in a seated position; a deformable shape sensing arrangement disposed on the seat portion of the chair-like base for measuring the three-dimensional contour of the seating support surface of a person seated thereon and for converting the three-dimensional contour to a two-dimensional format; a reference arrangement disposed on the chair-like base for measuring the three-dimensional contour relative to the back portion of the chair-like base; and a data recording device coupled to the shape sensing arrangement for recording a person's contour on a two-dimensional medium.

BRIEF DESCRIPTION OF THE DRAWINGS

The appended claims set forth those novel features which characterize the invention. However, the invention itself, as well as further objects and advantages thereof, will best be understood by reference to the following detailed description of a preferred embodiment taken in conjunction with the accompanying drawings, where like reference characters identify like elements throughout the various figures, in which:

DESCRIPTION OF THE PREFERRED EMBODIMENT

Figure 1:
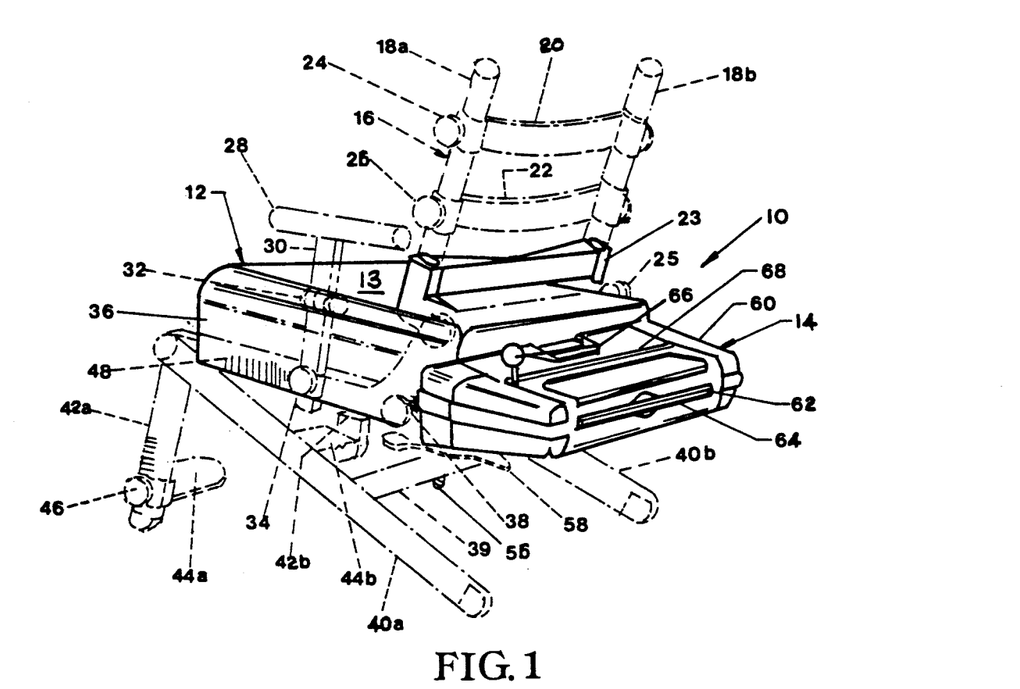
FIG. 1 is a perspective view of a mechanical shape sensor and data recorder disposed in a support base in accordance with the principles of the present invention.

Referring to FIG. 1, there is shown a perspective view of a mechanical shape sensor and data recorder 10 in accordance with the principles of the present invention. The mechanical shape sensor and data recorder 10 is positioned on and coupled to a chair-like base 16 shown in dotted-line form. The mechanical shape sensor and data recorder arrangement 10 includes a mechanical shape sensor 12 disposed in the seat portion of the chair-like base 16 and a data recorder 14 extending aft of the chair-like base.

The chair-like base 16 includes left and right upright back supports 18a and 18b, where the terms "left" and "right" are taken from the perspective of a person seated on the chair-like base. Disposed between and coupled to the upright back supports 18a, 18b are an upper cross member 20, a lower cross member 22, and a fixed, or reference, cross member 23. The upper cross member 20 is coupled to the upright back supports 18a, 18b by means of a pair of positioning knobs 24 to allow the height of the upper cross member to be adjusted depending on the size of the person seated on the chair-like base 16. Similarly, lower cross member 22 is coupled to the upright back supports 18a, 18b by means of a pair of positioning knobs 26 to allow its position along the upright back supports to be adjusted depending on the size of the person seated on the chair-like base 16. Reference cross member 23 is fixedly attached to upright back supports 18a, 18b and provides a reference from which points on the mechanical shape sensor 12 may be measured. Thus, a person seated in the chair-like base 16 is positioned so that his or her lower back engages the reference cross member 23 to provide a reference for the various points on the upper surface of the mechanical shape sensor 12 at which the person's seating surface contour is measured. The back support portion of the chair-like base 16 is coupled to the seat portion thereof by means of a pair of positioning knobs 25 to allow the angle of inclination of the back support portion to be adjusted relative to the seat portion.

The seat portion of the chair-like base 16 includes a seat frame 48 for receiving and supporting the mechanical shape sensor 12. Attached to lateral portions of seat frame 48 are left and right arm rests, with only the left arm rest 28 shown in the figure for simplicity. Arm rest 28 is supported by and attached to seat frame 48 by means of an arm rest support member 30. Arm rest support member 30 includes a positioning knob 32 along the length thereof for adjusting the angle between upper and lower portions of the arm rest support member to allow for adjustment of the distance between the left and right arm rests. Positioning knob 32 thus permits spacing between the arm rests to be adjusted depending upon the width of the person seated on the chair-like base 16. A lower positioning knob 34 attaches arm rest support member 30 to seat frame 48 in a manner which permits the height of arm rest 28 to be adjusted, as desired. A similar positioning knob combination is provided for the right arm rest, although these details of the invention are not shown in the figure for simplicity.

Seat frame 48 is coupled to and supported by left and right forward legs 42a and 42b and left and right aft legs 40a and 40b. Extending between and connecting the left and right aft legs 40a, 40b is a lower cross member 39. Lower cross member 39 is coupled to an aft portion of seat frame 48 by means of the combination of a threaded member 56 and a wing nut 58. Rotation of wing nut 58 causes a corresponding translation of threaded member 56 permitting the spacing between lower cross member 39 and seat frame 48 to be adjusted, as desired It is in this manner that the inclination of the chair-like base 16 may be adjusted in accordance with the preference of a person using the mechanical shape sensor and data recorder 10. Left and right foot supports 44a and 44b are respectively disposed on the left and right forward legs 42a, 42b. Rotational positioning knobs 46 are used to attach the foot supports 44a, 44b to the forward legs 42a, 42b, as shown for the case of the left foot support and left forward leg. Positioning knob 46 allows the height of each foot support to be adjusted along the length of its associated forward leg depending upon the leg dimensions of a person seated on the chair-like base 16. Seat frame 48 receives and provides support for the combination of a seat cushion 13 and a seat cushion frame 36.

Data recorder 14 includes a housing 60 having an upper slot 68 and an aft slot 64. Disposed in and moveable along upper slot 68 is a handle 66. Handle 66 is disposed on an upper portion of a data recording mechanism 70 shown in a perspective view in FIG. 2. Data recording mechanism 70, the configuration and operation of which is described in detail below, is disposed within the data recorder housing 60. Inserted in the aft slot 64 is a data sheet 62 also as described in detail below. Housing 60 is preferably comprised of coupled upper and lower portions to permit the housing to be opened to gain access to the data recording mechanism 70 for maintenance and/or replacement. Housing 60 may be comprised of a material such as plastic, while the chair-like base 16 is preferably comprised of metal primarily.

Figure 3:
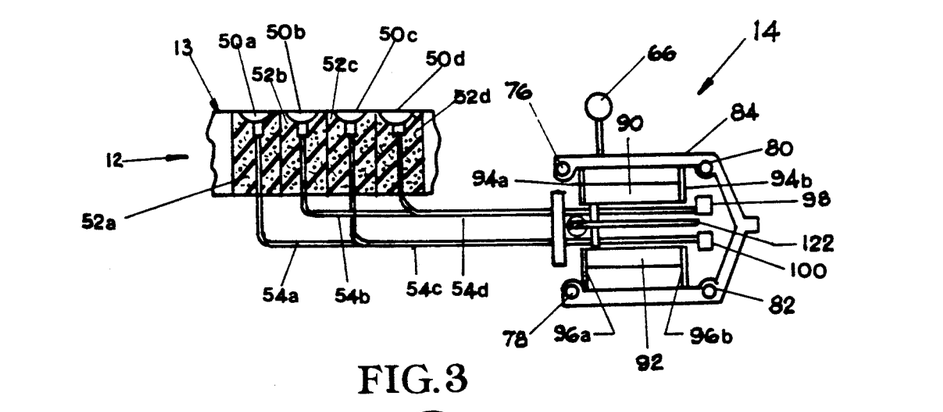
FIG. 3 is a simplified lateral sectional view showing details of the interconnection between the mechanical shape sensor and the data recorder.

Referring to FIG. 3, there is shown a simplified lateral sectional view of the mechanical shape sensor 12 and the data recorder 14 as well as their interconnection. Mechanical shape sensor 12 includes a plurality of resilient, compressible elements 52a-52d arranged in a matrix array as described in aforementioned U.S. Pat No. 4,998,354, the disclosure of which is incorporated by reference in the present application. When a person sits on the foam seat cushion 13 shown in FIG. 1 which is comprised of the plurality of resilient, compressible elements 52a-52d, as shown in FIG. 3, the upper surface of various of the resilient, compressible elements will be displaced downward as pressure is applied to these elements. The contour of the upper surface of foam seat cushion 13 as determined by the amount of deflection downward of each of the resilient, compressible elements 52a-52d provides an accurate representation of the contour of the person's thighs and buttocks or the dorsal and lateral surfaces of a person's trunk.

Disposed in the upper surface of each of the resilient, compressible elements 52a-52d are respective cushion surface sensor caps 50a-50d. Each of the cushion surface sensor caps 50a-50d, which are described in detail below, is positioned within and is displaced with the upper surface of its associated resilient, compressible element. Thus, with a person seated on the resilient, compressible elements 52a-52d, each of the cushion surface sensor caps 50a-50d will be deflected downwardly. Attached to each of the cushion surface sensor caps 50a-50d is a respective incompressible, flexible cable 54a-54d. The opposed ends of each of the cables 54a-54d are each attached to a respective marker element (which is not shown in FIG. 3 for simplicity) as described below.

Figure 2:
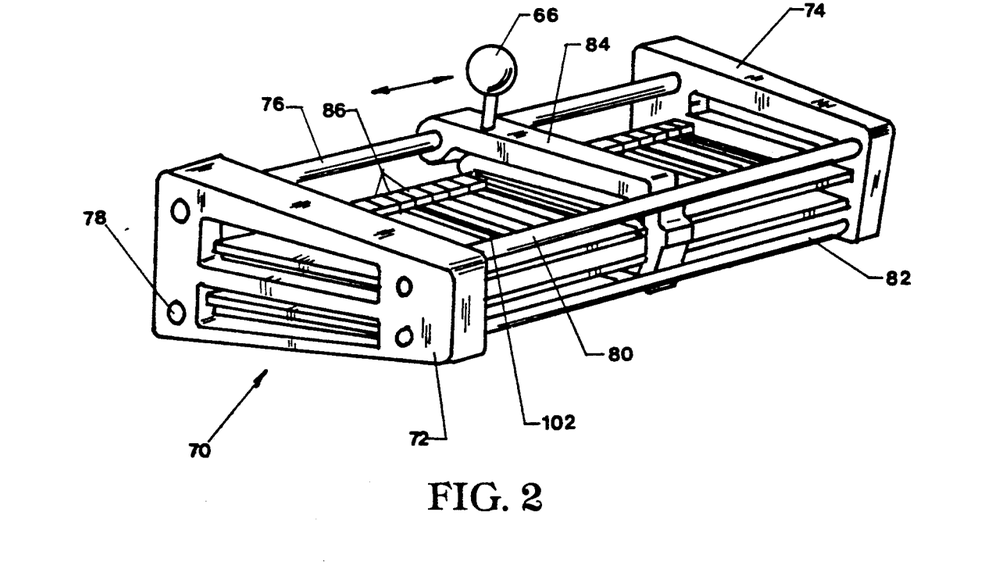
FIG. 2 is a perspective view of a data recording mechanism for use in the mechanical shape sensor and data recorder of the present invention.
Figure 4:
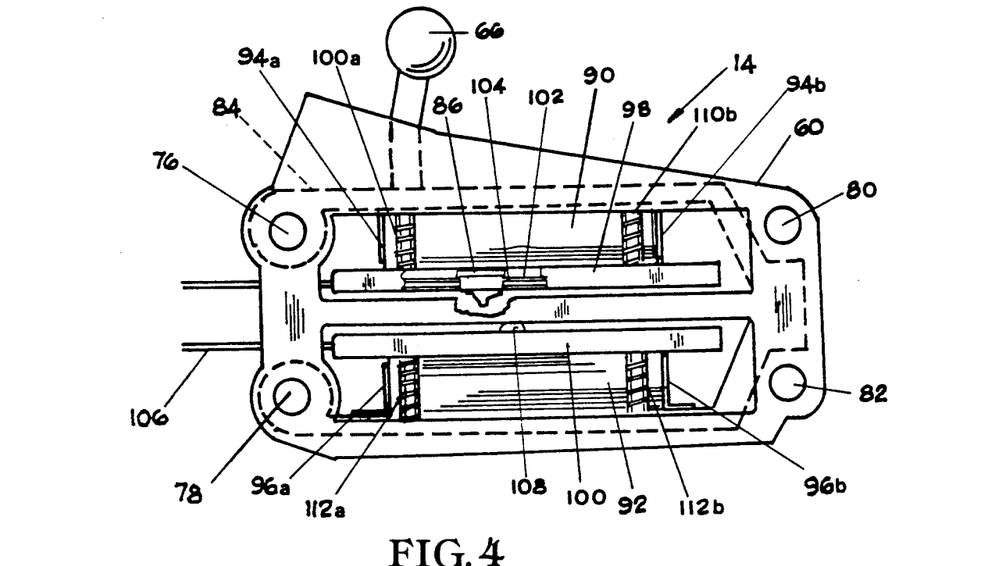
FIG. 4 is a side elevation view shown partially cutaway and partially in phantom of the data recorder including the data recording mechanism of FIG. 2.

With reference to FIGS. 2 and 4, the operation and configuration of the data recording mechanism 70 disposed within the data recorder 14 will now be described. Data recording mechanism 70 includes left and right support brackets 72 and 74. Connecting the left and right support brackets 72, 74 are upper and lower roller guides 76 and 78 and upper and lower alignment bars 80 and 82. The combination of the left and right support brackets 70,74, upper and lower roller guides 76, 78 and upper and lower alignment bars 80, 82 form a rigid, generally rectangular frame. The upper and lower roller guides 76, 78 are inserted through respective apertures in a generally C-shaped moveable guide bracket 84. Moveable guide bracket 84 is freely moveable along the lengths of the upper and lower roller guides 76, 78. Disposed on an upper portion of the moveable guide bracket 84 is a handle 66 which extends out through the upper slot 68 within the housing 60 of the data recorder 14. Handle 66 permits guide bracket 84 to be manually displaced along the length of the data recording mechanism 70.

Extending downward from an upper portion of guide bracket 84 are a first pair of upper mounting brackets 94a and 94b. Coupled to and supported by the upper mounting brackets 94a, 94b is an upper roller 90. Extending upward from a lower portion of guide bracket 84 are a second pair of lower mounting brackets 96a and 96b. Disposed between and supported by the lower mounting brackets 96a, 96b is a lower roller 92. Upper and lower rollers 90, 92 respectively engage a plurality of upper and lower data markers 86 and 108 as guide bracket 84 is manually displaced along the length of the data recording mechanism 70. The upper and lower data markers 86, 108 are each arranged in a generally planar array.

The upper and lower pluralities of data markers 86 and 108 are each coupled to a respective one of upper and lower displacement cables 104 and 106. Each of the upper and lower displacement cables 104, 106 is, in turn, coupled at its opposite end to a respective one of the cushion surface sensor caps as described above and is illustrated in FIG. 3. A plurality of upper alignment tubes 102 and lower alignment tubes (which are not shown in the figures for simplicity) are arranged within respective upper and lower frames 98 and 100 disposed within the data recording mechanism 70.

Figures 7, 8, 9:
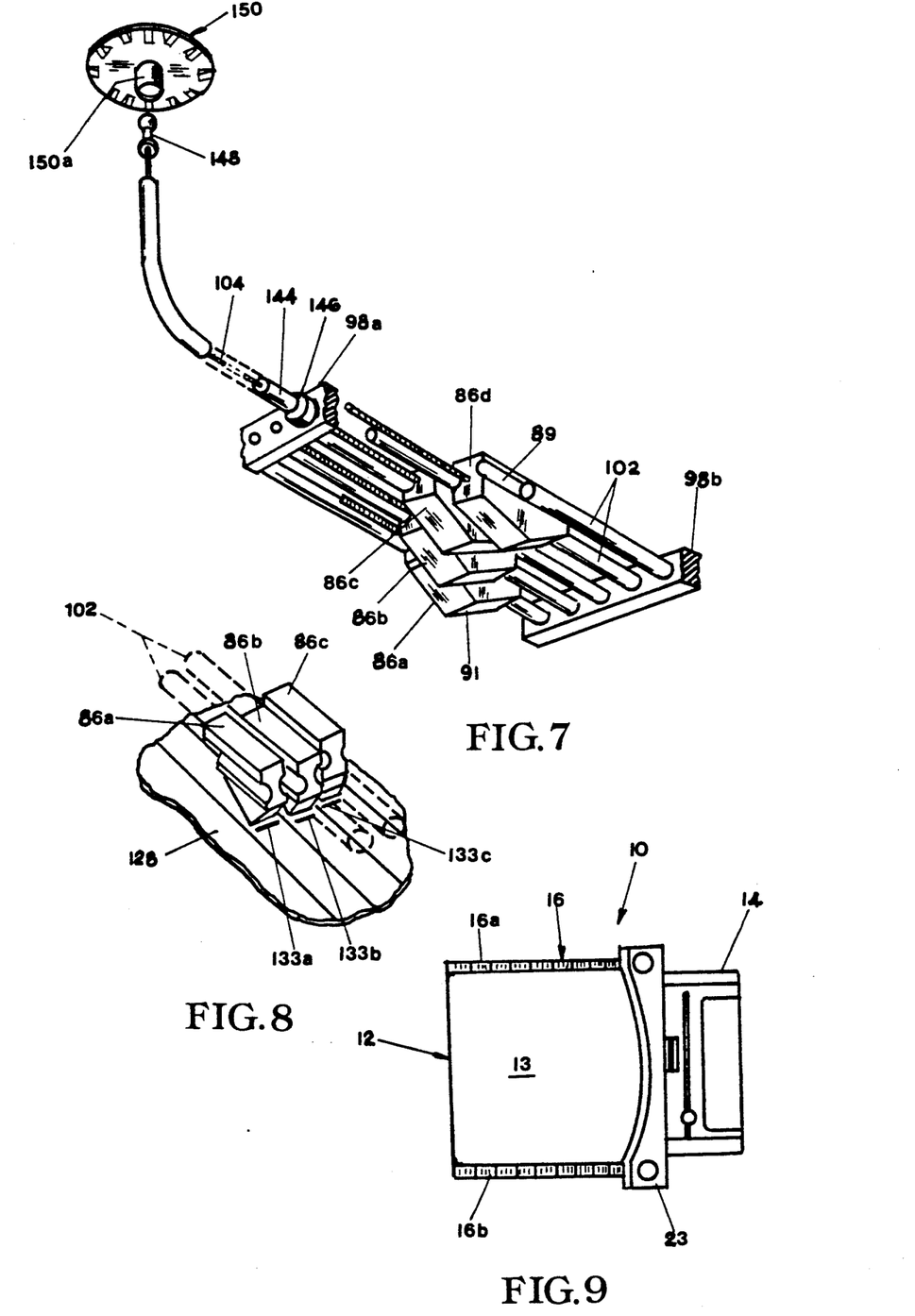
FIG. 7 is a lower perspective view of a portion of the mechanical shape sensor and data recorder illustrating the manner in which three-dimensional contour data is converted to a two-dimensional format.
FIG. 8 is a perspective view of a portion of the data recorder illustrating the shape and position of the data recording elements and the data points made by these elements.
FIG. 9 is a plan view of the mechanical shape sensor and data recorder shown in FIG. 1.

The position of the upper alignment tubes 102 relative to the upper data markers 86a-86d within the upper frame 86 is shown in the lower perspective view of a portion of the data recording mechanism shown in FIG. 7. Each of the data markers 86a–86d is attached to one end of a respective one of the cables 104 and is moveable therewith. Each of the data markers 86a–86d has a pair of lateral slots 89 disposed on opposed surfaces thereof. An upper alignment tube 102 is inserted within each of the lateral slots 89 on both sides of each of the upper data markers 86a–86d. The upper data markers 86a–86d are free to move along a respective pair of adjacent upper alignment tubes 102 which provide support for the data marker. Each of the upper alignment tubes 102 is securely attached at respective ends thereof to upper frame members 98a and 98b for mounting in the upper frame 98. Upper alignment tubes 102 ensure that all of the upper data markers 86a–86d are displaced generally parallel and prevent any transverse displacement of the data markers relative to the respective cable to which it is attached. Upper alignment tubes 102 thus ensure accurate positioning of data marks on the data sheet by each of the upper data markers 86a–86d by preventing any bending or lateral displacement of the upper displacement cables 104 to which the data markers are attached. A similar arrangement is provided for in the lower frame 100 of the data recording mechanism 70 which supports and allows for linear, generally parallel displacement of each of the lower data markers 108. As described above, the upper surface of each of the upper data markers 86 and the lower surface of each of the lower data markers 108 is adapted for engagement with the upper and lower rollers 90, 92, respectively, for urging the generally planar arrays of data markers toward each other and into engagement with the data sheet. The generally C-shaped moveable guide bracket 84 provides a rigid coupling between the upper and lower rollers 90, 92 and maintains the rollers a fixed distance apart. By preventing displacement of the upper and lower rollers 90, 92 away from one another, a fixed pressure is applied to the upper and lower data markers 86, 108 regardless of the pressure applied by an operator. The data marks formed are thus independent of applied operator pressure for more accurate data recording. The pressure applied to the data markers is also independent of the tracking force for moving the rollers across the data markers.

Also as shown in FIG. 7, a cushion surface sensor cap 150 is coupled to one end of displacement cable 104 by means of a ball joint connector 148. Ball joint connector 148 is inserted in a socket 150a disposed on a lower portion of the cushion surface sensor cap 150. Ball joint connector 148 permits free pivoting displacement of the cushion surface sensor cap 150 on the end of displacement cable 104 and allows the cushion surface sensor cap to assume the orientation of the contour at a given location on the upper surface of the foam seat cushion 13 without applying a bending load to the cable to which the cap is attached as in prior approaches. By permitting each cushion surface sensor cap 150 to closely assume the orientation of a given point on the upper surface of the foam seat cushion 13 and avoiding bending of the cable to which the cap is attached, the position of data markers 186a–186d attached to the other end of displacement cables 104 more accurately represents the contour of the foam seat cushion. In addition, each cushion surface sensor cap 150 is easily removed from its associated cable by merely pulling it off the ball joint connector 148 rather than unscrewing it as in prior art approaches. This arrangement facilitates replacement of the foam seat cushion 13 which loses its resilience with time and extended use and must be replaced. Each of the cables 104 extends from the upper frame 98 through a respective routing tube 144 coupled at one end thereof by means of a connector 146 to an upper frame member 98a.

Upper frame 98 is coupled to the left and right support brackets 72 and 74 by means of a plurality of connecting pin and coiled spring combinations, where two such combinations identified as elements 110a and 110b connecting the upper frame to the left support bracket are shown in FIG. 4. Similarly, lower frame 100 is coupled to the left and right support brackets 72, 74 by means of a plurality of connecting pin and coiled spring combinations 112a and 112b. Each of the upper and lower frames 98, 100 are maintained in position by a plurality of the aforementioned connecting pins and are urged toward each other by the aforementioned plurality of coiled springs. This arrangement maintains the upper and lower frames 98, 100 in proper spacing from a data card inserted between the upper and lower frames as described below. Proper spacing between the upper and lower frames 98, 100 and the data sheet ensures that all data markers engage the data sheet when the upper and lower rollers 90, 92 are displaced over the data markers such that all data points are recorded and no data is lost.

Figure 5:
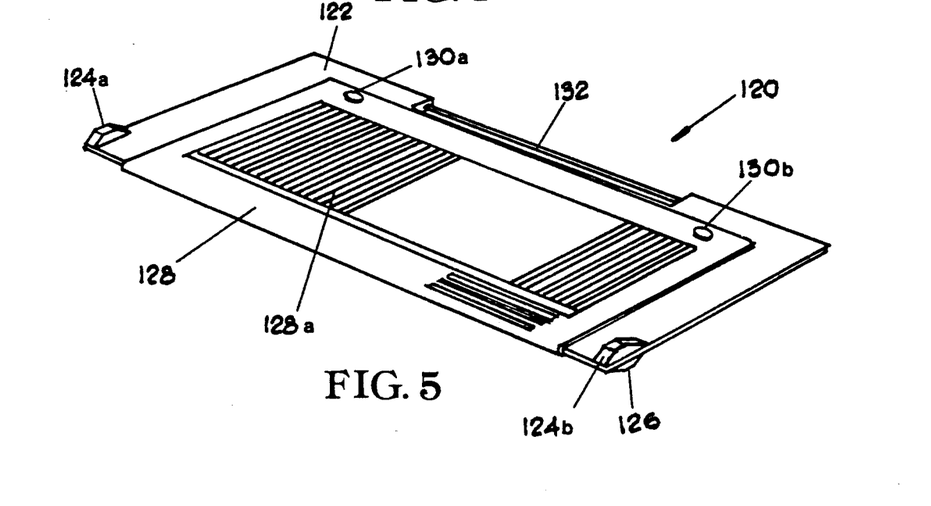
FIG. 5 is a perspective view of a data recording medium for use in the data recording mechanism of FIG. 2.

Referring to FIG. 5, there is shown a perspective view of a graphic recording arrangement 120 for use in the data recorder 14. The graphic recording arrangement 120 includes a generally planar platen, or data board, 122 having opposed, generally flat surfaces. Platen 122 is adapted for insertion in and removal from data recorder 14 via the aft slot 64 in data recorder housing 60 shown in FIG. 1. An aft edge of platen 122 is provided with a flexible handle, or grip, 132 for facilitating manual insertion of the graphic recording arrangement 120 in the data recorder 14, and its removal therefrom.

Platen 122 is adapted to receive a folded data sheet, or form, 128. With data sheet 128 folded, upper and lower data entry portions of the sheet are respectively disposed on the upper and lower surfaces of platen 122, with the upper data entry portion 128a shown in FIG. 5. Disposed on platen 122 are a plurality of spaced locators, or alignment markers, 130a and 130b which are adapted for insertion in respective corresponding apertures in data sheet 128 to ensure proper positioning and alignment of the data sheet relative to platen. Proper positioning and alignment of data sheet 128 on platen 122 ensures proper location of the contour data marks on the upper and lower data entry portions of the data sheet by the upper and lower arrays of data markers. Data sheet 128 is preferably comprised of a pressure-sensitive, self-adhesive material which is responsive to engagement by the aforementioned data markers and adheres to platen 122 once positioned thereon.

Disposed on opposed, leading edges of platen 122 are a pair of upper frame separators 124a and 124b and a pair of lower frame separators, only one of which is shown in FIG. 5 as element 126. Upon insertion of the leading edge of platen 122 over which data sheet 128 is folded, the upper frame separators 124a, 124b engage upper frame 98 and displace it upwardly as the platen is inserted in the data recording mechanism 70. Similarly, the lower frame separators 126 engage and downwardly displace lower frame 100. Thus, the upper frame separators 124a, 124b overcome the downward biasing of upper frame 98 by coiled springs 110a and 110b and urge the upper frame in an upward direction. Similarly, the lower frame separators 126 overcome the upward urging of the lower frame 100 by coiled springs 112a and 112b in displacing the lower frame in a downward direction. In this manner, the upper and lower frames 98, 100 as well as the upper and lower ar rays of data markers 86 and 108 are displaced away from one another as platen 122 is inserted in the data recording mechanism 70. Upward and downward displacement of the upper and lower data markers 86, 108 prevents their engagement with the pressure-sensitive data sheet 128 as the data sheet and platen 122 are inserted in the data recording mechanism 70 to prevent unwanted marking of an erroneous data entry on the data sheet as it is inserted into or removed from the data recording mechanism. With platen 122 fully inserted in data recording mechanism 70, the upper frame separators 124a, 124b as well as the lower frame separators 126 extend beyond the upper and lower frames 98, 100 allowing the aforementioned coiled springs urging the frames together to again establish proper spacing of the upper and lower data markers 86, 108 relative to the data sheet and platen combination.

Figure 6:
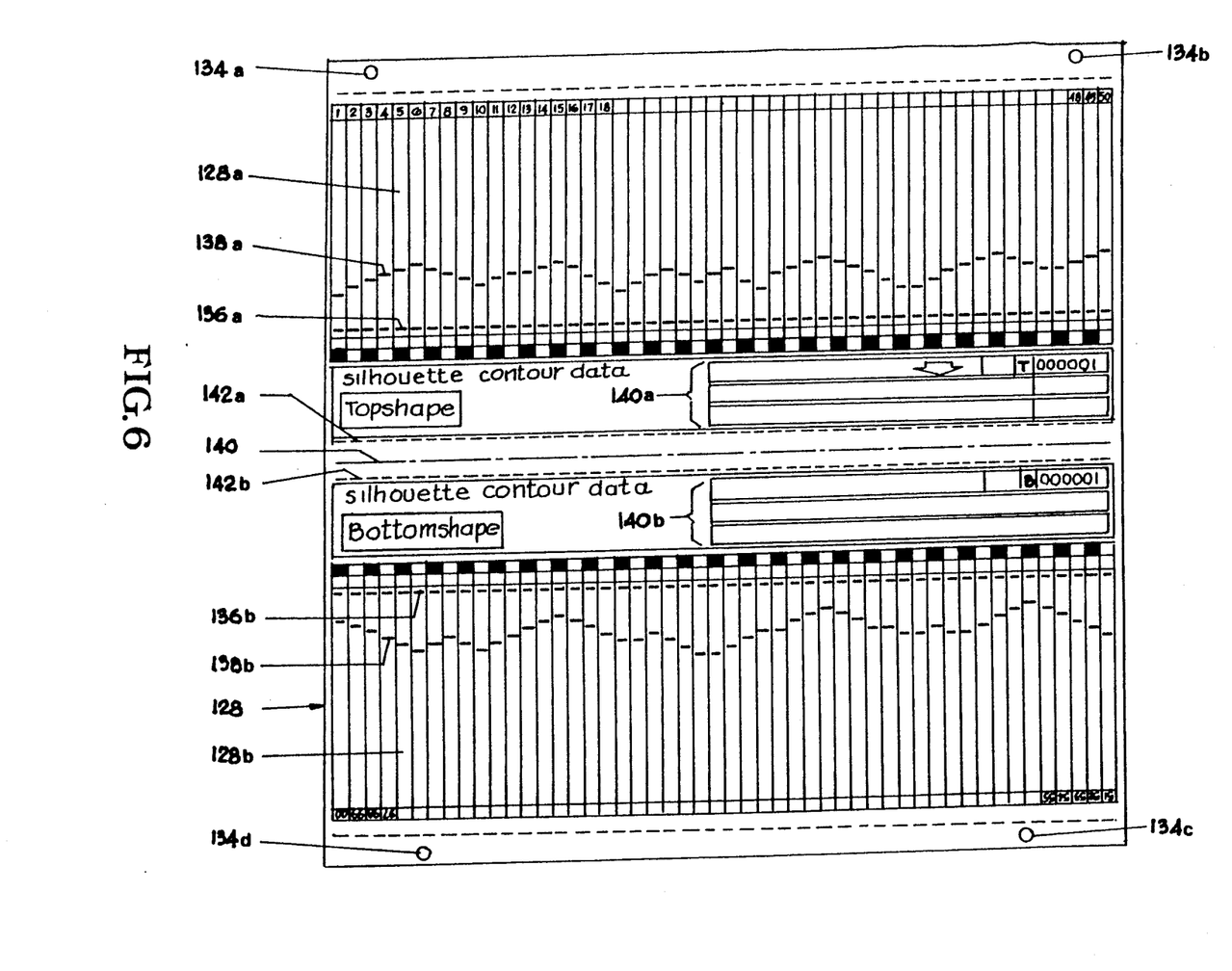
FIG. 6 is a plan view of a data recording form for use in the data recording mechanism of FIG. 2.

Referring to FIG. 6, there is shown a data sheet 128 for use in the mechanical shape sensor and data recorder of the present invention. Data sheet 128 is adapted for folding along center fold line 140. With data sheet 128 folded along line 140, the data sheet is divided into first and second data entry portions 128a and 128b. First and second data entry portions 128a, 128b are adapted for positioning on respective opposed, generally flat surfaces of platen 122, with fold line 140 disposed adjacent to a forward edge of the platen as previously described. First data entry portion 128a includes a pair of spaced alignment apertures 134a and 134b, while the second data entry portion 128b includes a corresponding pair of alignment apertures 134d and 134c. Alignment apertures 134a-134d ensure proper positioning and an alignment of data sheet 128 with platen 122. First and second data entry portions 128a, 128b of data sheet 128 further include respective data entry blocks 140a and 140b for entering information relating to the person whose seating contour surface is being measured and recorded. After recording contour data on the first and second data entry portions 128a, 128b of data sheet 128, the two data entry portions are separated by tearing along first and second perforated tear lines 142a and 142b. The first and second data entry portions 128a, 128b are then particularly adapted for transmitting the contour data such as via a telecommunications link to a central location for reading the recorded contour data and forming a custom contoured seat cushion in accordance therewith.

The first data entry portion 128a includes first and second sets of data points 136a and 138a. Similarly, the second data entry portion 128b also includes first and second sets of data points 136b and 138b. Each of the first set of data points 136a, 136b is in the form of a linear array of individual data marks along the lengths of the first and second data entry portions 128a, 128b. Each of the first sets of data points 136a, 136b are formed without a person positioned on the mechanical shape sensor 12 prior to measuring the seating surface contour of a person. These first sets of data points 136a, 136b are formed by displacing the upper and lower rollers 90, 92 over the upper and lower data markers 86, 108 for urging the data markers into contact with the first and second data entry portions 128a, 128b of the data sheet 128 as previously described. Data points 136a and 136b thus represent a reference contour of the mechanical shape sensor 12 for calibrating the mechanical shape sensor and data recorder 10. Once calibrated, a person to be measured is seated on the mechanical shape sensor 12 and again the upper and lower rollers 90, 92 are displaced over the upper and lower arrays of data markers 86, 108 so as to form first and second sets of contour data points 138a and 138b respectively on the first and second data entry portions 128a, 128b of data sheet 128. The displacement between each contour data point and its associated calibration data point represents the extent of deflection of a cushion surface sensor cap in one of the resilient, compressible elements forming the foam seat cushion 13. The displacement between the upper and lower contour data points 138a, 138b and their respective calibration data points 136a, 136b provides a highly accurate measure of the contour of the upper surface of the foam seat cushion 13 with a person seated thereon. As shown in the figure, there are 50 data points on each of the first and second data entry portions 128a, 128b of data sheet 128. Each of the numbered data points corresponds with a given location on the foam seat cushion 13, where the data points are arranged in a cyclic manner in accordance with the number of support elements in a given row within the matrix of resilient, compressible elements in the foam seat cushion. This cyclic arrangement of marker elements as described in aforementioned U.S. Pat. No. 4,998,354 converts the three-dimensional contour support surface of a person sitting on the array of resilient, compressible support elements into two dimensions in a format which is easily recorded and reproduced for fabricating a custom contoured seat cushion.

Referring to FIG. 8, there is shown a perspective view of a portion of a data sheet 128 illustrating the shape and position of three data markers 86a, 86b and 86c and the corresponding data marks 133a, 133b and 133c which these markers impress on the data sheet. As shown in the figure, each of the three data markers 86a, 86b and 86c includes a pair of lateral slots on opposing sides thereof. An alignment tube 102 (shown in dotted-line form) is disposed intermediate adjacent data markers and is positioned within adjacent slots in each of the markers. Thus, a pair of adjacent alignment tubes 102 engage each of the data markers 86a, 86b and 86c. The data markers 86a, 86b and 86c are displaced along the length of the alignment tubes 102. When displaced toward data sheet 128 by a roller, as previously described, each of the data markers 86a, 86b and 86c engages and impresses an associated data mark 133a, 133b and 133c on the data sheet. The generally V-shaped tip on each of the data markers 86a, 86b and 86c results in the formation of a thin, elongated data mark, where the short dimension of the mark is aligned with the direction of displacement of the data marker. This provides for highly accurate data recording with position errors minimized because of the short dimension of the data mark along the direction of displacement of the data marker and its associated cushion surface sensor cap disposed in the upper surface of the foam seat cushion 13.

Referring to FIG. 9, there is shown a plan view of the mechanical shape sensor and data recorder 10. As shown in the figure, the foam seat cushion 13 disposed in the mechanical shape sensor 12 is generally rectangular and is positioned forward of the data recorder 14. The reference cross-member 23 is disposed above an aft portion of the foam seat cushion 13. The position of the reference cross-member 23 relative to the mechanical shape sensor 12 is determined by right and left base rulers 16a and 16b. Numerical scales on the right and left base rulers 16a, 16b provide a highly accurate indication of the forward and aft position of the reference cross-member 23 relative to the mechanical shape sensor 12. With the position of the reference cross-member 23 precisely determined with respect to the mechanical shape sensor 12 and its foam seat cushion 13, the location of the measured seating surface contour of a person positioned on the foam seat cushion relative to the reference cross-member 23 and the back portion of the chair-like base 16 is precisely known. This ensures proper positioning of the individually contoured seat cushion in the base for which it is intended such as a wheelchair.

There has thus been shown a mechanical shape sensor and data recorder for measuring the three-dimensional seating contour surface of a person in the seated position and for recording the contour data in a two-dimensional format on a data sheet. The contour data on the data sheet can then be transmitted such as by telecommunications link to a central location for the fabrication of a custom contoured seat cushion. The mechanical shape sensor and data recorder is adapted for installation in a chair-like base for measuring and recording a seat surface contour in the environment in which the resulting custom contoured cushion will be used, such as in a wheelchair. The mechanical shape sensor and data recorder provides highly accurate seat surface contour measurements, is easily used, maintained and transported, and is relatively inexpensive.

While particular embodiments of the present invention have been shown and described, it will be obvious to those skilled in the art that changes and modifications may be made without departing from the invention in its broader aspects. Therefore, the aim in the appended claims is to cover all such changes and modifications as fall within the true spirit and scope of the invention. The matter set forth in the foregoing description and accompanying drawings is offered by way of illustration only and not as a limitation. The actual scope of the invention is intended to be defined in the following claims when viewed in their proper perspective based on the prior art.

We claim:

1. Apparatus for measuring and recording the contour of a person's seating support surface, said apparatus comprising:
   a chair-like base having a seat portion and a back portion for respectively supporting a person's thighs and buttocks and a person's back when in a seated position;
   deformable shape sensing means disposed on said seat portion of said chair-like base for measuring the three-dimensional contour of the seating support surface of a person seated thereon and for converting said three-dimensional contour to a two-dimensional format;
   reference means disposed on said chair-like base for measuring the three-dimensional contour relative to said back portion of said chair-like base, said reference means including fixed cross-member means in said back portion for engaging and supporting only the lower back of a person seated on said chair-like base, said reference means further including means for measuring the relative positions of said seat and back portions of said base; and
   recording means coupled to said shape sensing means for recording a person's contour on a two-dimensional medium.

2. The apparatus of claim 1 wherein said chair-like base includes means for adjusting the relative positions of said seat and back portions.

3. The apparatus of claim 2 wherein said chair-like base further includes means for engaging and supporting the arms and feet of a person seated on said base.

4. The apparatus of claim 3 wherein said chair-like base further includes means for adjusting the positions of said means for engaging and supporting the arms and feet of a person seated on said base.

5. The apparatus of claim 1 wherein said means for measuring the relative positions of said seat and back portions includes a ruler disposed on said seat portion for indicating the position of said back portion on said seat portion.

6. The apparatus of claim 1 wherein said two-dimensional medium includes at least one pressure-sensitive data sheet and said recording means includes at least one data sheet engaging means for applying pressure to said data sheet for recording a person's contour in a two-dimensional format.

7. The apparatus of claim 6 wherein said deformable shape sensing means includes a plurality of compressible, resilient support elements disposed in a closely spaced, matrix array on said seat portion of said chair-like base.

8. The apparatus of claim 7 wherein said deformable shape sensing means further includes a plurality of surface sensor elements each disposed in an upper surface of one of said support elements, a plurality of data markers for engaging said pressure-sensitive data sheet, and means for coupling each surface sensor element to a respective one of said data markers.

9. The apparatus of claim 8 wherein said means for coupling said surface sensor elements and said data markers includes a plurality of flexible, incompressible cables, with each cable coupling a respective surface sensor element to its associated data marker.

10. The apparatus of claim 9 further comprising a plurality of alignment tubes engaging each of said data markers for preventing lateral displacement and ensuring parallel displacement of said data markers.

11. The apparatus of claim 10 wherein each data marker includes a generally V-shaped tip for engaging said pressure-sensitive data sheet, and wherein said V-shaped tip has a long dimension and a short dimension, with said short dimension aligned along the direction of displacement of said data marker.

12. The apparatus of claim 11 further comprising means for inserting and removing said data sheet from said recording means.

13. The apparatus of claim 12 wherein said data sheet is foldable into two sections for recording contour data and said means for inserting and removing said data sheet includes a generally flat platen having first and second opposed sides each adapted to receive and support a section of said foldable data sheet.

14. The apparatus of claim 13 further comprising means for preventing engagement of said data markers with said data sheet during insertion of and removal of said platen and data sheet from said recording means.

15. The apparatus of claim 13 further comprising positioning means disposed on said platen for ensuring proper positioning of said data sheet on said platen.

16. The apparatus of claim 13 further comprising gripping means disposed on said platen for facilitating manual insertion and removal of said data sheet from said data recorder.

17. The apparatus of claim 13 wherein said recording means includes first and second generally planar, spaced arrays of said data markers for respectively engaging said first and second folded sections of said data sheet.

18. The apparatus of claim 17 wherein said data sheet engaging means includes first and second spaced, moveable rollers for respectively engaging and displacing said first and second spaced arrays of data markers in engagement with said first and second folded sections of said data sheet, respectively.

19. The apparatus of claim 18 further comprising rigid means for securely coupling said first and second rollers and preventing their relative movement toward or away from one another.

20. The apparatus of claim 19 further comprising a handle coupled to said rigid means to facilitate manual displacement of said first and second rollers over said first and second arrays of data markers.

21. The apparatus of claim 20 further comprising means for urging said first and second arrays of data markers toward said first and second folded sections of said data sheet, respectively.

22. The apparatus of claim 21 wherein said means for urging said first and second arrays of data markers toward said first and second folded sections of said data sheet includes a plurality of coiled springs.

23. The apparatus of claim 22 further comprising means for calibrating the contour data recorded on said data sheet.

24. The apparatus of claim 23 further comprising pivoting coupling means for coupling each of said surface sensor elements to its associated cable for permitting said surface sensor element to assume the orientation of the upper surface of its associated support element.

25. The apparatus of claim 24 wherein said pivoting coupling means includes a ball joint connector.

26. Data recording apparatus for recording the seat support contour of a seated person's thighs and buttocks or the dorsal and lateral surfaces of the person's trunk, said data recording apparatus comprising:
   a frame;
   first and second spaced, generally planar arrays of moveable position markers coupled to said frame, wherein the position of each of said position markers represents a position of a corresponding location on the person's seat support contour;
   first and second rollers respectively disposed adjacent said first and second planar arrays of said position markers, wherein said first and second planar arrays of said position markers are disposed intermediate said first and second rollers;
   moveable guide means coupled to said first and second rollers for moving said first and second rollers across and in engagement with said first and second planar arrays of said position markers, whereby said first and second arrays of said position markers are urged toward each other;
   a generally planar platen removably disposed intermediate said first and second arrays of said position markers; and;
   a pressure-sensitive data sheet disposed on opposed generally planar surfaces of said platen, wherein said first and second arrays of data markers engage said data sheet when urged toward each other by said first and second rollers for recording data marks representing a person's seat support contour on said data sheet.

27. The apparatus of claim 26 further comprising a plurality of alignment tubes coupled to said frame and engaging each of said data markers for preventing lateral displacement and ensuring parallel displacement of said data markers.

28. The apparatus of claim 27 wherein each data marker includes a generally V-shaped tip for engaging said pressure-sensitive data sheet, and wherein said V-shaped tip has a long dimension and a short dimension, with said short dimension aligned along the direction of displacement of said data marker.

29. The apparatus of claim 28 further comprising means for inserting and removing said data sheet from said recording means.

30. The apparatus of claim 29 wherein said data sheet is foldable into two sections for recording contour data and said means for inserting and removing said data sheet includes said platen having first and second opposed sides each adapted to receive and support a section of said foldable data sheet.

31. The apparatus of claim 30 further comprising means for preventing engagement of said data markers with said data sheet during insertion of and removal of said platen and data sheet from said data recording apparatus.

32. The apparatus of claim 30 further comprising positioning means disposed on said platen for ensuring proper positioning of said data sheet on said platen.

33. The apparatus of claim 30 further comprising gripping means disposed on said platen for facilitating manual insertion and removal of said data sheet from said data recorder.

34. The apparatus of claim 26 further comprising a handle coupled to said moveable guide means to facilitate manual displacement of said first and second rollers over said first and second arrays of data markers.

35. The apparatus of claim 34 further comprising means for urging said first and second arrays of data markers into engagement with said first and second folded sections of said data sheet, respectively.

36. The apparatus of claim 35 wherein said means for urging said first and second arrays of data markers into engagement with said first and second folded sections of said data sheet includes a plurality of coiled springs.

37. The apparatus of claim 26 further comprising means for calibrating the contour data recorded on said data sheet.

* * * * *

UNITED STATES PATENT AND TRADEMARK OFFICE
CERTIFICATE OF CORRECTION

PATENT NO. : 5,193,285
DATED : March 16, 1993
INVENTOR(S) : Heinrich et al.

It is certified that error appears in the above-indentified patent and that said Letters Patent is hereby corrected as shown below:

Abstract,

14th Line: "locatin" should be --location--.

| COLUMN | LINE | |
|---|---|---|
| 5 | 22 | Insert --.--, after "desired". |
| 9 | 6 | "ar rays" should be --arrays--. |

Signed and Sealed this

Eighteenth Day of January, 1994

Attest:

BRUCE LEHMAN

Attesting Officer     Commissioner of Patents and Trademarks